(12) United States Patent
Daly et al.

(10) Patent No.: US 8,680,852 B2
(45) Date of Patent: Mar. 25, 2014

(54) METHOD AND APPARATUS FOR PHASE SENSITIVE DETECTION OF EDDY CURRENT MEASUREMENTS

(75) Inventors: Alan Daly, Luton (GB); Xiaoyu Qiao, Hatfield (GB); Ian Christopher Mayes, Ampthill (GB); John Hansen, Harpenden (GB)

(73) Assignee: GE Inspection Technologies Ltd., Bedfordshire (GB)

( * ) Notice: Subject to any disclaimer, the term of this patent is extended or adjusted under 35 U.S.C. 154(b) by 750 days.

(21) Appl. No.: 12/866,536

(22) PCT Filed: Feb. 6, 2009

(86) PCT No.: PCT/GB2009/050119
§ 371 (c)(1),
(2), (4) Date: Aug. 6, 2010

(87) PCT Pub. No.: WO2009/101431
PCT Pub. Date: Aug. 20, 2009

(65) Prior Publication Data
US 2010/0327860 A1    Dec. 30, 2010

(30) Foreign Application Priority Data
Feb. 15, 2008  (GB) .................................. 0802850.8

(51) Int. Cl.
*G01N 27/82*  (2006.01)
(52) U.S. Cl.
USPC ......................................... 324/240; 324/235

(58) Field of Classification Search
USPC .......................................................... 324/240
See application file for complete search history.

(56) References Cited

U.S. PATENT DOCUMENTS

| 4,207,520 A | | 6/1980 | Flora et al. | |
|---|---|---|---|---|
| 4,325,257 A | * | 4/1982 | Kino et al. | ...................... 73/626 |
| 4,486,713 A | | 12/1984 | Gifford | |
| 4,630,229 A | * | 12/1986 | D'Hondt | ....................... 708/405 |
| 4,965,761 A | * | 10/1990 | Schlunt | ......................... 708/405 |
| 6,734,669 B2 | | 5/2004 | Lopez | |

FOREIGN PATENT DOCUMENTS

| EP | 1211859 A2 | 6/2002 |
|---|---|---|
| EP | 1887352 A2 | 2/2008 |

* cited by examiner

*Primary Examiner* — Arleen M Vazquez
*Assistant Examiner* — Alesa Allgood
(74) *Attorney, Agent, or Firm* — Global Patent Operation; Mark A. Conklin

(57) ABSTRACT

A method of detecting defects using eddy currents is disclosed. The method comprises:
 exciting eddy currents in a test material using an eddy current probe driven by a drive signal;
 detecting induced eddy currents in the test material;
 converting the detected signal into integer values using an analog to digital converter; and
 adding or subtracting the generated integer values to or from each of two accumulators, or taking no action, so that one accumulator produces a value proportional to one component of the detected signal and the other produces a value proportional to another component of the detected signal and using these values to detect the presence of a defect.

19 Claims, 4 Drawing Sheets

Fig. 4a
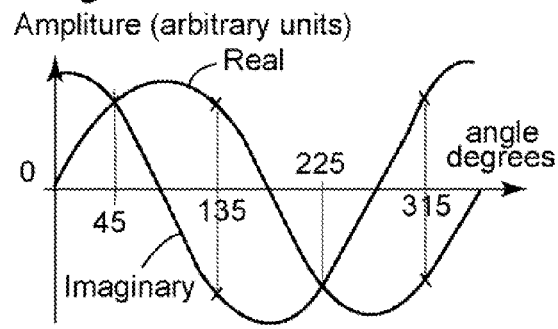
Fig. 4b
Fig. 5a
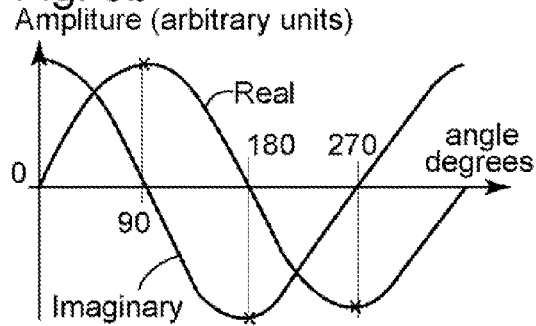
Fig. 5b
Fig. 6a
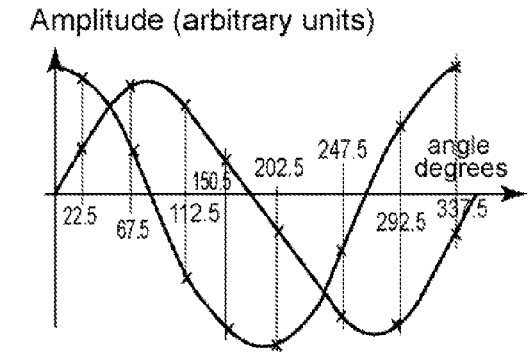
Fig. 6b

METHOD AND APPARATUS FOR PHASE SENSITIVE DETECTION OF EDDY CURRENT MEASUREMENTS

BACKGROUND TO THE INVENTION

Eddy Current (EC) instruments are typically used to detect defects, such as cracks and thinning in electrically conductive structures, usually made from metals or to measure material properties such as conductivity and permeability, which in turn are related to hardness and material structure. All of these are observed by monitoring the change in the magnitude and phase of magnetically induced eddy currents. A drive coil that produces an alternating magnetic field is generally provided close to a test piece to induce current in the test piece. The presence of defects disrupts the circulating Eddy Currents. Eddy currents can, be sensed by picking up their magnetic field or by measuring the change of impedance of the drive coil.

There are many arrangements for inducing and sensing eddy currents, but in nearly every case there is a need to measure the phase and amplitude relationship between the sensed and drive signal. This can be done either digitally or by using analogue methods. Often the change in the sensed signal due to a defect is small and electrical noise can mask the measurement. In some cases it is necessary to remove effects on the signal due to other parts of the structure, such as supports. This is often done using multi-frequency drive currents, in which one or more of the frequencies is sensitive to the defect and the others are largely only affected by the support structure.

To achieve good detectivity the instrument has to have both good amplitude and phase discrimination for both single and multi-frequency signals. FIG. 1 shows one way of doing this. A received signal 1 is multiplied by a sine function 2 and a cosine function 3, followed by a low pass filter 4 to obtain the real 5 and imaginary 6 components respectively. These can then either be used directly in a complex impedance plane view of the data or with a little additional computation the phase and amplitude data can be obtained from these numbers.

The multiplication of the signal is readily performed using analog multipliers or can be done digitally using a fast processing device such as an FPGA. Digital methods have the advantage that once the signal has been digitized there are no offset and phase errors. In analog systems the physical components used in the separate real and imaginary signal processing paths will have small differences that result in errors that can be temperature and time dependent.

U.S. Pat. No. 4,207,520 discloses a multiple frequency digital eddy current inspection system. Received eddy current signals from a test coil are filtered to select a desired signal which is changed into a digital signal and passed to a computer for processing and to provide results of the eddy current inspection.

U.S. Pat. No. 6,734,669 discloses digital demodulation of an eddy current signal. Digital sine and cosine functions are generated and multiplied with a digitized received signal. The eddy current signal is isolated by filtering the mixed signal with a low pass filter.

SUMMARY OF THE INVENTION

According to a first aspect of the present invention, there is provided a method of detecting defects using eddy currents, the method comprising:

exciting eddy currents in a test material using an eddy current probe;

detecting induced eddy currents in the test material;

converting the detected signal into integer values using an analog to digital convertor; and either adding or subtracting the generated integer values to or from each of two accumulators or taking no action, so that one accumulator produces a value proportional to the real component and the other produces a value proportional to the imaginary component. These values are used to detect the presence of a defect.

Embodiments of this invention provide a method that has advantages inherent to digital methods with the simplicity of an analogue switching method. Unlike prior methods that use multiplication followed by low pass filtering, our method is a single step process using just addition and subtraction to an accumulator and is capable of being carried out without the need for floating point arithmetic, using just simple integer mathematics.

The simplicity of the method means that it can be performed at a very fast rate and that it can, if required, be carried out using less power hungry and lower cost logic and is therefore also suitable for battery power operation.

Most FPGA devices have a limited number of multipliers. Most of the space is occupied by gates that can easily be arranged for simple addition operations and storage and so are well suited to implement examples of the present invention.

Each generated integer value is added to or subtracted from each accumulator according to the status of the accumulators flag.

The status of this flag (Add, Subtract or take no action) is pre-defined and forms part of a repeated series.

Each accumulator has its own pre-defined, repeated series. The repeated series for each of the accumulators is identical except one is shifted by a quarter of a cycle with respect to the other.

According to a second aspect of the present invention there is provided an apparatus for detecting defects using eddy currents, the apparatus comprising:

a detector for detecting induced eddy currents in a test material;

a converter for converting the detected signal into integer values; and a controller for adding or subtracting the generated integer values to or from each of two accumulators, so that the accumulators produce values indicative of whether or not a defect is present.

BRIEF DESCRIPTION OF THE DRAWINGS

Embodiments of the present invention will now be described, by way of example only, with reference to the accompanying drawings, in which:

FIGS. 4a and 4b show a table and corresponding waveform of a first set of sampling positions;

FIGS. 5a and 5b show a second table and corresponding waveform for a second set of sampling intervals;

FIGS. 6a and 6b show a third table and corresponding waveform for a third set of sampling intervals;

DETAILED DESCRIPTION OF THE INVENTION

Figure 1:
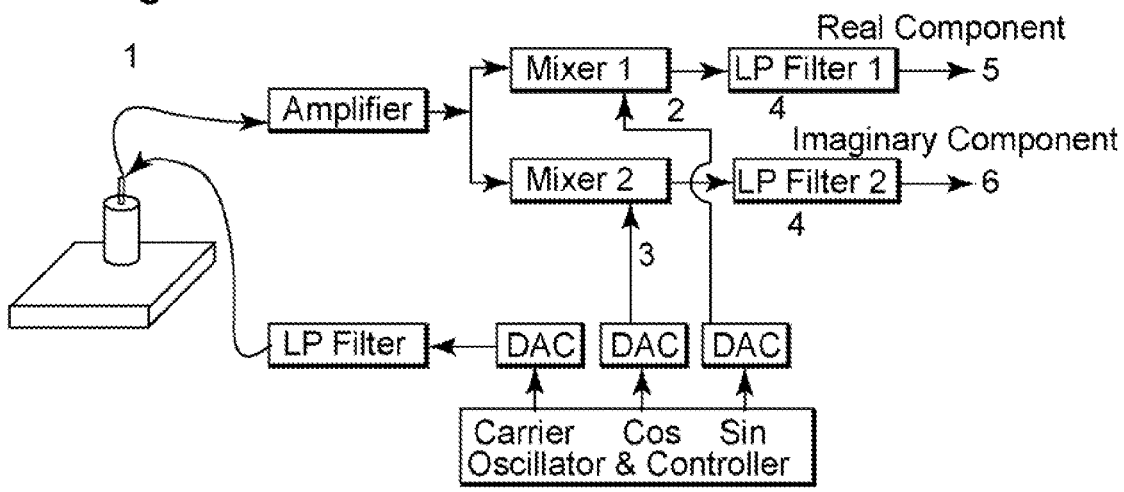
FIG. 1 illustrates amplitude and phase discrimination for a prior art instrument.
Figure 2:
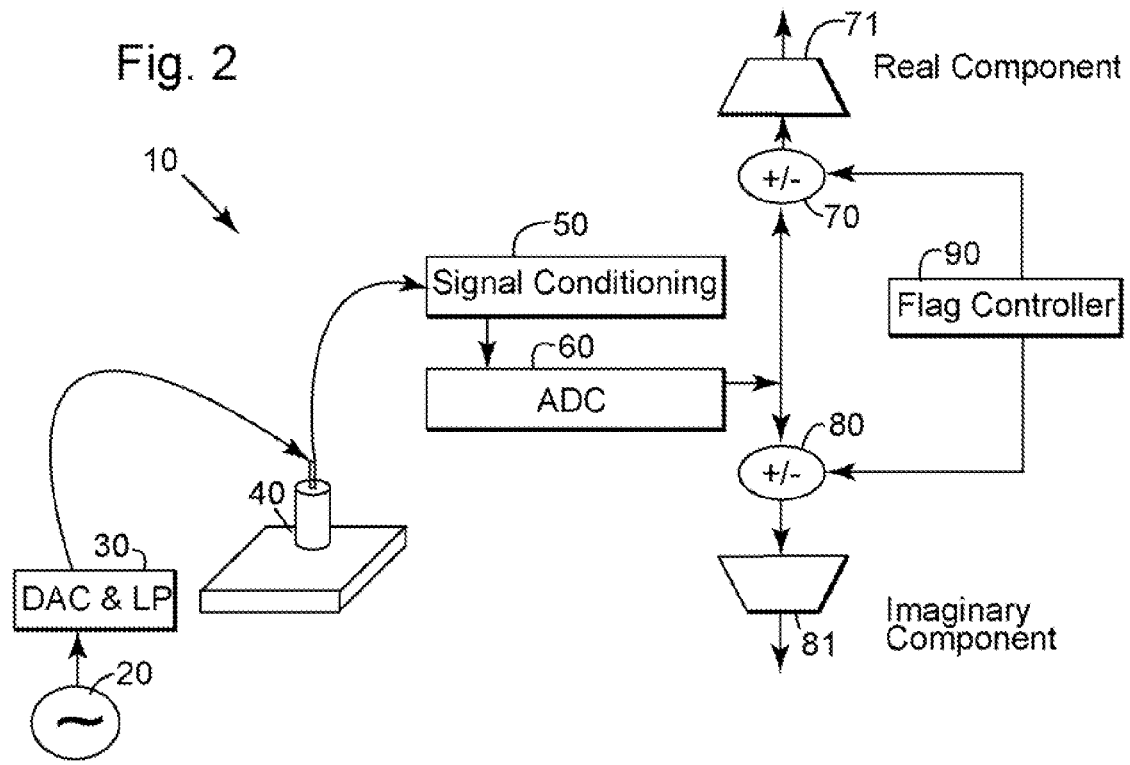
FIG. 2 illustrates an example of an embodiment of the present invention.

FIG. 2 shows an eddy current instrument 10 embodying the present invention. In this example a drive signal is synthesized from one or more sinusoidal waves generated by an oscillator 20. The digitally synthesized drive signal is passed to a digital to analog converter and low pass filter 30 and used to excite eddy currents in a test piece via a suitable probe 40.

Induced eddy currents from the test piece are then detected using a sensing device. The sensing device may comprise sensing the current in the exciting coil or coils or may be a secondary magnetic field sensing device, such as one or more coils, GMR or Hall effect sensors where the sensing device may be incorporated in the exciting probe 40 or can be separate from it.

The sensed signal is then conditioned by being passed through a suitable signal conditioner 50. The signal conditioner 50 typically performs one or more of amplification, pre-filtering and in some cases where high defect detectivity is required, subtraction of a reference signal.

The conditioned signal is then converted into an integer value, in this example using an analog to digital (A/D) converter 60. The waveform generator 20, analog to digital converter 60 and subsequent de-modulation using controller 90 may each be driven by the same clock signal to ensure that they are synchronised.

The integer values generated by the analog to digital converter 60 are added to or subtracted from 70,80 each of two accumulators 71,81 controlled by the controller 90. Each accumulator 71,81 is arranged to provide a rolling average of a predetermined number of integer numbers generated by the analog to digital converter 60. The controller 90 determines and controls whether the generated integer numbers are added to or subtracted from the running total of each accumulator 71, 81 or whether no action is taken with regard to a particular generated integer number. The controller 90 is arranged such that one accumulator 71 is arranged to provide an output value proportional to the real component of the sensed signal and the other accumulator 81 is arranged to provide a value proportional to the imaginary component of the sensed signal. A master clock (not shown) ensures that the waveform generation 20, analog to digital conversion 60 and subsequent de-modulation 70,71,80,81,90 are synchronised with each other.

If the drive signal contains more than one frequency component, then the circuit 10 may be duplicated for each of the frequency components and the controller 90 arranged to control the addition, subtraction or no action according to the selected frequency component.

The real and imaginary components for each drive signal frequency can be displayed as complex impedance planes, as a function of time or as a function of position for an operator to detect defects, when in use. The ability to detect defects may be enhanced by subtracting reference values obtained from measurements made on a defect free part of the test piece or by way of suitable calibration.

If required, phase and amplitude data for each of the drive signal frequencies can be calculated from the real and imaginary components for suitable presentation to an operator.

Whether the controller 90 adds, subtracts or takes no action regarding a generated integer value with respect to each of the accumulators 71,81 is discussed in more detail later. Each generated integer value is added to or subtracted from each accumulator according to the status of the accumulators flag. The status of this flag (Add, Subtract or take no action) is pre-defined and forms part of a repeated series. Each accumulator 71,81 has its own pre-defined, repeated series. The repeated series for each of the accumulators is identical except the series for accumulator 81 is shifted by a quarter of a cycle with respect to the series for accumulator 71.

Figure 3:
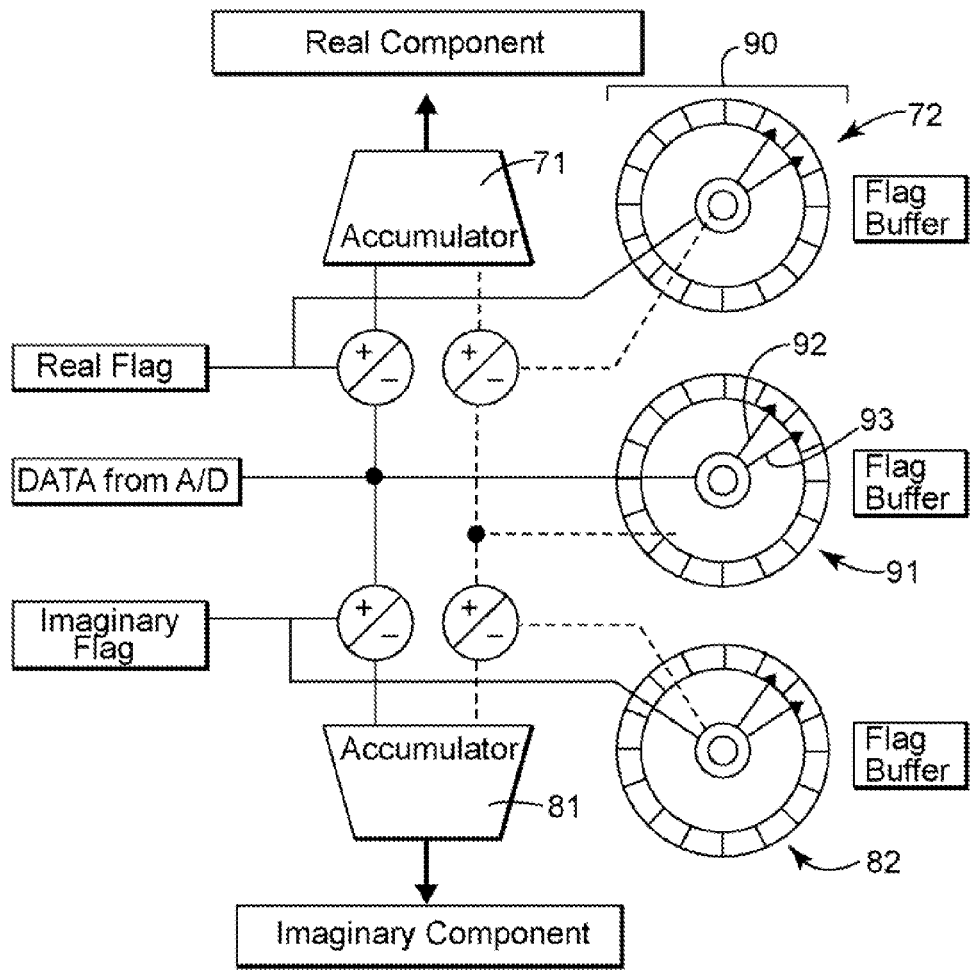
FIG. 3 illustrates a more detailed example of an embodiment of the present invention.

FIG. 3 shows a preferred example of the controller 90, the accumulators 71,81 and the data buffer 91. Each of the real and imaginary components is obtained by adding or subtracting data received from the analog to digital converter 60 to the real accumulator 71 and imaginary accumulator 81 according to the status of a respective "real flag" and "imaginary flag". The status of each flag (add, subtract or take no action) is generated by suitable logic. This logic sets flags to add, subtract or take no action in accordance with a flag buffer 72,82 which stores the sequence of add, subtract or take no action flags forming a cycle for each accumulator 71,81.

Control logic within the controller 90 sets flags within each of the flag buffers 72,82 to add when a generated integer value is to be added to an accumulator 71,81, to subtract when a generated integer value is to be subtracted from an accumulator 71,81 or is set such that neither addition nor subtraction takes place.

Each accumulator 71,81 generates a rolling average over a predetermined number of generated integer values or measurement points. The precise number of generated integer values selected for the rolling average depends upon a number of factors including but not limited to the frequency of the probe drive signal, clock frequency and the level of noise rejection required. For example, if the rolling average is arranged to use 200 generated integer values, circular flag buffers 72,82 each able to store 200 add, subtract, or "no action" flags are provided and a circular byte buffer 91 with 200 memory locations is provided to store the generated integer values. As each generated integer value from the analog to digital converter 60 is added to or subtracted from each accumulator 71,81, it is also stored in the byte buffer 91 and the buffer pointer 92 is incremented to the next location. A second pointer 93, one memory location ahead points to the tail end value, and this value is removed from each accumulator 71,81. Removal involves performing the opposite operation from that done originally i.e. if the generated integer value was originally added to the accumulator 71,81, it is now subtracted. If the value was originally subtracted from the accumulator 71,81, it is now added. If no action was taken, then no action is taken to reverse it. In order to do this, the add, subtract and "no action" flags are stored in the circular flag buffers 72,82 which are similar to the byte buffer 91 used to store the generated integer values. Instead of using flag buffers 72,82 the add, subtract and "take no action" flags may be regenerated using suitable counters (not shown) which may be preferred as it uses less logic, reducing hardware costs and power consumption.

FIGS. 4a, 4b, 5a, 5b, 6a and 6b illustrate how the addition, subtraction and "no action" flags are determined. As explained above, each flag buffer 72,82 contains a cycle of addition and subtraction and possibly "no action" flags. Each cycle comprises at least one series of one or more additions and at least one series of one or more subtractions, possibly also with "no action" flags. Each generated integer value is added to or subtracted from each accumulator 71,81 to form a running average. The repeated series for each of the accumulators is identical except the series for accumulator 81 is shifted by a quarter of a cycle with respect to the series for accumulator 71. This is illustrated in the examples below.

FIG. 4b illustrates a "real" sinusoidal signal and an "imaginary" sinusoidal signal. As can be seen the real sinusoidal signal is displaced from the imaginary sinusoidal cycle by a quarter of a cycle or 90°. Sample points corresponding to the point at which integer values are generated by the analog to digital converter 60 may be selected at any convenient interval. In the example of FIG. 4a and FIG. 4b generated integer values are sampled at 45°, 135°, 225° and 315°. As can be seen, the real and imaginary flags are selected to be "add" or "subtract" dependent upon whether the corresponding real and imaginary sinusoidal signals are positive or negative at that particular sampling angle.

FIGS. 5a and 5b illustrates the same number of sampling points as in FIGS. 4a and 4b, except in this example samples are taken at 0°, 90°, 180° and 270°. As can be seen, samples taken when the real or imaginary sinusoidal signal crosses the horizontal axis, do not generate either an addition or subtraction flag. In this situation a "no action taken" flag (0 in the table of FIG. 5a) is instead generated signifying that the particular generated integer value from the analog to digital converter 60 that is generated at this sample point is neither added to nor subtracted from the accumulator.

FIGS. 6a and 6b provide still more sampled values producing even more precise and accurate results.

Figure 7:
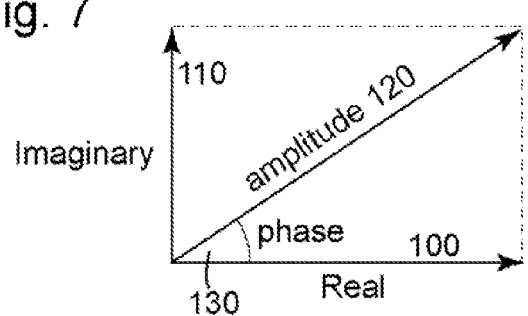
FIG. 7 illustrates conversion from real and imaginary components to amplitude and phase values.

At the foot of each table in FIGS. 4a, 5a and 6a is provided a correction factor. This can be used to compute the true real and imaginary components of the signal by dividing by the number of samples and then multiplying by the correction factor. The correction factor for the real component is obtained by summing the absolute sine values corresponding to the position of the measurement points in a single sinusoidal cycle and dividing by the number of points. The correction factor for the imaginary component is obtained by summing the absolute cosine values corresponding to the measurement points in a single sinusoidal cycle and dividing by the number of points. In most cases the real and imaginary values generated are used directly by an operator to detect defects, generally by presenting these values on a viewing screen. However, the amplitude and phase of the sensed signal may be determined from the real and imaginary components as illustrated in FIG. 7. Since the real component 100 and imaginary component 110 are orthogonal vectors, the resultant amplitude 120 may be calculated by determining the square root of the sum of the square of the real component 100 and the imaginary component 110 by applying the Pythagoras rule. The phase angle 130 of the sensed signal is determined by calculating the arctangent of the imaginary component 110 divided by the real component 100.

Although any number of sample points may be taken in each sinusoidal cycle of the drive signal, it has been found that using an integer number of sample points in each cycle of the drive signal and an integer number of sinusoidal cycles averaged by the accumulator produces superior results. It has been found preferable to use an integer number of sample points especially when less samples are taken per sinusoidal cycle of the drive signal.

As explained above it is preferable that the analog to digital converter 60 is synchronized with the drive waveform 20 to provide consistent results.

As explained above, in some situations it is preferable to take measurements with multiple simultaneous drive frequencies. In this situation, the real and imaginary components for each of the drive frequencies may be extracted. When multiple simultaneous drive frequencies are used, the frequencies are preferably selected such that the higher frequencies are not odd integer multiples of lower frequencies i.e. not 1:3, 1:5 etc. Avoiding odd integer multiples of lower frequencies has been found to provide superior results. This is believed to be a consequence of Fourier harmonics. When using multiple drive frequencies it has been found that superior results are obtained when the same number of integer values are generated for each drive frequency and that the number of values represents an integer number of sinusoidal cycles in each case.

Figure 8A:
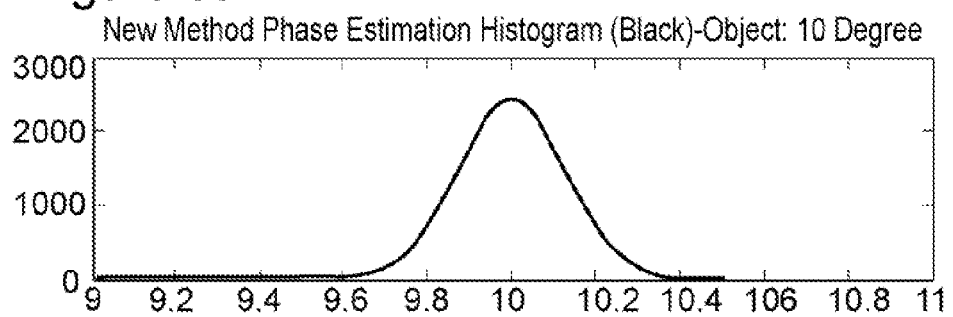
FIGS. 8a, 8b, 9a and 9b show histograms comparing results from an embodiment of the present invention compared to a conventional instrument.
Figure 8B:
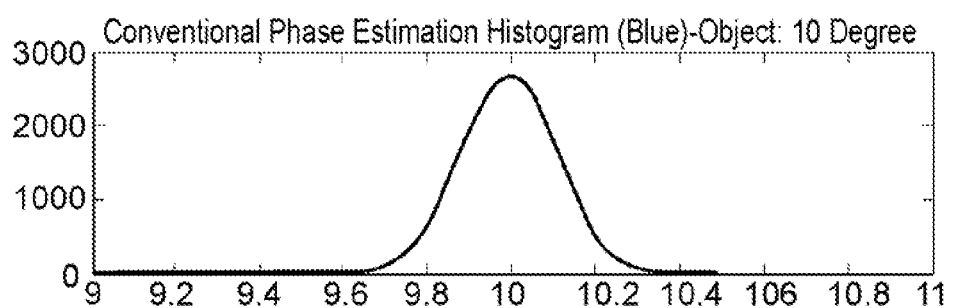
Figure 9A:
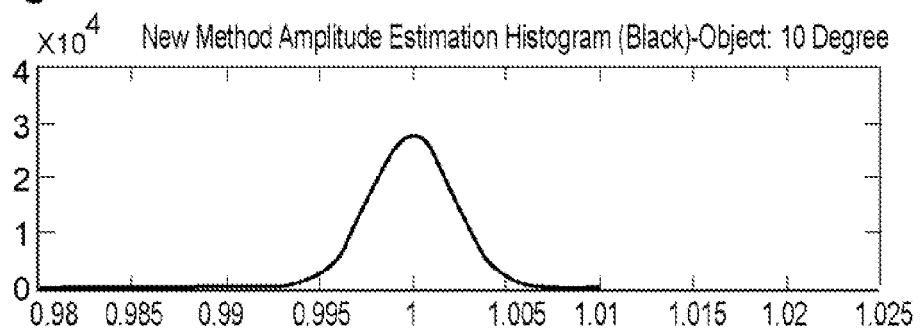
Figure 9B:
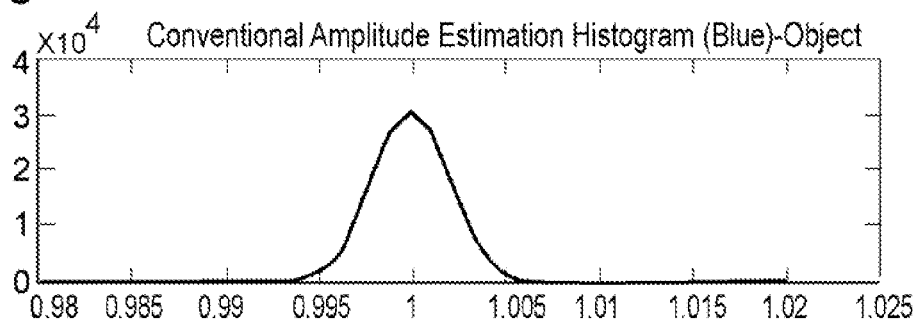

FIGS. 8a and 8b illustrate a comparison of the measurement of phase using a method in accordance with the present invention (FIG. 8a) compared to a measurement from the same sample using a conventional method. Likewise, FIG. 9a shows the results of the measurement of amplitude using a method in accordance with an embodiment of the present invention whilst FIG. 9b shows the amplitude results from the same sample using a conventional method. As can be seen, the quality of the results is equivalent. However, the simplicity of the method of examples of the present invention enables it to be performed at a faster rate and enables it to be carried out on hardware using less power hungry and lower cost logic and is therefore suitable for use with battery power operation.

It has been found that superior results are obtained when results are balanced. Balancing is a process in which the signal from a part of the test piece without a defect is subtracted from the measurements. This difference signal can then be amplified, making better use of the analog to digital converter 60 and thus improving detectivity. In practical terms, balancing can be achieved by using an appropriate differential probe or by injection of a balance signal into the signal conditioning electronics 50. Alternatively, the signal may be balanced by digital subtraction of the output from the analog to digital converter 60.

Many variations may be made to the examples described above whilst still falling within the scope of the present invention. For example, instead of the flag buffers 72,82 shown in FIG. 3, other logic or suitable counters may be used.

The invention claimed is:

1. A method of detecting defects using eddy currents, the method comprising:
    exciting eddy currents in a test material using an eddy current probe driven by a drive signal;
    detecting induced eddy currents in the test material;
    converting the detected signal into integer values using an analog to digital converter; and
    adding or subtracting the generated integer values to or from each of two accumulators, or taking no action, so that one accumulator produces a value proportional to one component of the detected signal and the other produces a value proportional to another component of the detected signal and using these values to detect the presence of a defect, wherein each generated integer value is added to or subtracted from each accumulator according to the status of the accumulators flag, the status of each flag as add, subtract, or take no action being pre-defined and forming part of a repeated series.

2. A method according to claim 1, wherein each accumulator has its own pre-defined, repeated series of flags, the repeated series for each of the accumulators being identical except one is shifted by a quarter of a cycle with respect to the other.

3. A method according to claim 1, wherein an integer number of integer valves are generated by the analog to digital converter in each sinusoidal cycle of the drive signal.

4. A method according to claim 1, wherein the accumulators generate a rolling average over an integer number of sinusoidal cycles of the drive signal.

5. A method according to claim 1, wherein one accumulator produces a value proportional to the real component of the detected signal and the other accumulator produces a value proportional to the imaginary component of the detected signal.

6. A method according to claim 1, wherein the analog to digital converter is driven by a clock which is synchronized with the drive signal.

7. A method according to claim 1, wherein the eddy currents are excited in the test material using the eddy current probe driven at a plurality of simultaneous drive frequencies.

8. A method according to claim 1, wherein the eddy currents are excited in the test material using the eddy current probe driven at a plurality of sequential drive frequencies.

9. A method of detecting defects using eddy currents, the method comprising:
   exciting eddy currents in a test material using an eddy current probe driven by a drive signal;
   detecting induced eddy currents in the test material;
   converting the detected signal into integer values using an analog, to digital converter;
   adding or subtracting the generated integer values to or from each of two accumulators, or taking no action, so that one accumulator produces a value proportional to one component of the detected signal and the other produces a value proportional to another component of the detected signal and using these values to detect the presence of a defect; and
   wherein the eddy currents are excited in the test material using the eddy current probe driven at a plurality of simultaneous drive frequencies, and, wherein higher frequencies are selected such that they are not odd integer multiples of lower frequencies.

10. An apparatus for detecting defects using eddy currents, the apparatus comprising:
   a detector for detecting induced eddy currents in a test material;
   an analog to digital converter for converting the detected signal into integer values; and
   a controller for selectively adding some of the generated integer values to an accumulated total at one or both of the two accumulators and selectively subtracting some of the generated integer values from an accumulated total at one or both of the two accumulators, so that one accumulator produces a value proportional only to a real component of the detected signal and the other accumulator produces a value proportional only to an imaginary component of the detected signal and using these values to detect the presence of a defect.

11. An apparatus for detecting defects using eddy currents, the apparatus comprising:
   a detector for detecting induced eddy currents in a test material;
   an analog to digital converter for converting the detected signal into integer values; and
   a controller for adding or subtracting the generated integer values to or from each of two accumulators, or taking no action, so that one accumulator produces a value proportional to one component of the detected signal and the other produces a value proportional to another component of the detected signal and using these values to detect the presence of a defect, wherein the controller is arranged to add, subtract or take no action with respect to each generated integer value according to the status of each accumulator's flag, the status of each flag being pre-defined and forming part of a repeated series.

12. An apparatus according to claim 11, wherein each accumulator has its own pre-defined repeated series of flags, the repeated series of flags for each of the accumulators being identical except one is shifted by a quarter of a cycle with respect to the other.

13. An apparatus according to claim 11, wherein one accumulator produces a value proportional to the real component of the detected signal and the other accumulator produces a value proportional to the imaginary component of the detected signal.

14. An apparatus according to claim 11, further comprising an eddy current probe driven by a drive signal to generate the induced eddy currents in the test material.

15. An apparatus according to claim 14, wherein an integer number of integer valves are generated by the analog to digital converter in each sinusoidal cycle of the drive signal.

16. An apparatus according to claim 14, wherein the accumulators generate a rolling average over an integer number of sinusoidal cycles of the signal.

17. An apparatus according to claim 14, wherein the analog to digital converter is driven by a clock which is synchronized with the drive signal.

18. An apparatus according to claim 14, wherein the eddy currents are induced in the test material using the eddy current probe driven at a plurality of simultaneous drive frequencies.

19. An apparatus according to claim 14, wherein the eddy currents are induced in the test material using, the eddy current probe driven at a plurality of sequential drive frequencies.

* * * * *

UNITED STATES PATENT AND TRADEMARK OFFICE
CERTIFICATE OF CORRECTION

Page 1 of 1

PATENT NO.         : 8,680,852 B2
APPLICATION NO.    : 12/866536
DATED              : March 25, 2014
INVENTOR(S)        : Daly et al.

It is certified that error appears in the above-identified patent and that said Letters Patent is hereby corrected as shown below:

In the Specification

In Column 1, Line 18, delete "can," and insert -- can --, therefor.

In the Claims

In Column 7, Line 21, in Claim 9, delete "analog," and insert -- analog --, therefor.

In Column 8, Line 38, in Claim 16, delete "the signal." and insert -- the drive signal. --, therefor.

In Column 8, Line 46, in Claim 19, delete "using," and insert -- using --, therefor.

Signed and Sealed this
Fifteenth Day of September, 2015

Michelle K. Lee
*Director of the United States Patent and Trademark Office*